United States Patent [19]
Sun

[11] Patent Number: 5,940,175
[45] Date of Patent: Aug. 17, 1999

[54] METHOD AND APPARATUS FOR SURFACE INSPECTION IN A CHAMBER

[75] Inventor: James J. Sun, New Brighton, Minn.

[73] Assignee: MSP Corporation, Minneapolis, Minn.

[21] Appl. No.: 08/742,448

[22] Filed: Nov. 1, 1996

[51] Int. Cl.⁶ .................................................. G01N 21/00
[52] U.S. Cl. ........................................................ 356/237.3
[58] Field of Search .................................... 356/381–382, 356/237, 400, 343, 237.1–237.6, 445–448; 438/7, 16; 414/217, 806, 416, 811; 382/145; 216/60; 156/345; 250/574, 559.41; 118/719, 722, 725

[56] References Cited

U.S. PATENT DOCUMENTS

| | | |
|---|---|---|
| 3,790,287 | 2/1974 | Cuthbert et al. . |
| 3,931,525 | 1/1976 | Clarke . |
| 4,321,630 | 3/1982 | Kramer . |
| 4,378,159 | 3/1983 | Galbraith .............................. 356/237 |
| 4,508,450 | 4/1985 | Ohshima et al. ...................... 356/237 |
| 4,962,063 | 10/1990 | Maydan et al. . |
| 5,076,692 | 12/1991 | Neukermans et al. . |
| 5,083,035 | 1/1992 | Pecen et al. . |
| 5,176,493 | 1/1993 | Toro-Lira et al. . |
| 5,189,481 | 2/1993 | Jann et al. . |
| 5,220,405 | 6/1993 | Barbee et al. . |
| 5,258,824 | 11/1993 | Carlson et al. . |
| 5,259,881 | 11/1993 | Edwards et al. . |
| 5,270,222 | 12/1993 | Moslehi ...................................... 438/7 |
| 5,271,264 | 12/1993 | Chanayem . |
| 5,313,044 | 5/1994 | Massoud et al. . |
| 5,347,138 | 9/1994 | Aqui et al. . |
| 5,416,594 | 5/1995 | Gross et al. . |
| 5,450,205 | 9/1995 | Sawin et al. . |
| 5,465,154 | 11/1995 | Levy ..................................... 356/382 |

*Primary Examiner*—K. P. Hantis
*Attorney, Agent, or Firm*—Westman, Champlin & Kelly, P.A.

[57] ABSTRACT

An inspection system for inspecting products that have a flat, reflective surface, such as a wafer or a flat panel display on which a thin film is to be deposited, includes an inspection chamber connected to a processing chamber with both of the chambers being under vacuum. The inspection equipment performs the inspection with the product in the inspection chamber without removing the product from the vacuum environment. In a preferred form of the invention, the inspection chamber includes a wall portion that will transmit light, and the inspection equipment is a laser source directed to the reflective surface of the product and a receiver for receiving reflected light to determine changes in the character of the surface caused by the deposited film or by imperfections, haze or particles.

13 Claims, 8 Drawing Sheets

METHOD AND APPARATUS FOR SURFACE INSPECTION IN A CHAMBER

BACKGROUND OF THE INVENTION

The present invention relates to the measurement of contaminant particles deposited on a substrate and/or the measurement of deposition/etching film thickness on a substrate, such as a semiconductor wafer or the like, in a device fabrication process system during chemical vapor deposition (CVD), physical vapor deposition (PVD) or an etching process.

To control the quality of manufacturing, semiconductor wafers or the like are inspected for particles and defects by scanning the entire wafer surface with apparatus similar to that described in U.S. Pat. Nos. 4,378,159 to L. Galbraith, 5,076,692 to A. Neukermans et al., 5,083,035 to J. Pecen et al., 5,189,481 to P. Jann et al. and 5,416,594 to K. Gross et al. These methods require the wafer to be transferred from a process system, such as a PVD chamber, a CVD chamber or an etching chamber to a wafer scanner for inspection.

A process system for PVD, CVD or etching usually operates at a negative pressure (vacuum) ranging from one tenth of a millitorr to a few torr, while a wafer scanner typically operates at atmospheric pressure. Transporting wafers from a vacuum to atmospheric pressure and from room atmospheric pressure to a vacuum requires the use of a so called "load-lock" chamber device. The load-lock is an intermediate chamber which has two doors or gate valves, one connected to the vacuum process system and the other to ambient or room conditions. When a wafer or a set of wafers is loaded, the door of the load-lock chamber leading to the vacuum process system is closed, and the loading door to ambient is opened for wafer loading at ambient pressure. After loading, the loading door is closed and the load-lock chamber is pumped down to a vacuum level desired. When the pressure in the load-lock chamber is reduced to a level comparable to that in the process system, the exit door of the load-lock chamber to the process system is opened to allow the wafers to be transferred to the process system.

The pump down speed in the load-lock chamber is usually limited, because a high pump down rate may result in rapid changes in temperature as well as pressure. Rapid temperature change will cause vapor condensation to form contaminant particles. A typical pump down process may take up to a few minutes to complete. For comparison, the deposition time is much shorter. Typical metallic films and dielectric films may have a film thickness ranging from one hundred to a few thousand angstroms and typical deposition rates of a PVD or CVD process range from a few hundred to a few thousand angstroms per minute. The deposition time for such a film thickness in a typical PVD or CVD process is, therefore, on the order of under one minute or so.

Although a slow pump down speed can avoid vapor condensation and particle nucleation in load-locks, the speed is often set at or close to the highest tolerable limit in order to reduce the pump down time. The high pump down speed desired for efficiency increases the risk of forming contaminant particles in the load-lock, thus increasing the risk of wafers being contaminated during their transfer through a load-lock.

Advanced processing systems often have multiple deposition or etching chambers operated under the same, or similar vacuum conditions. One example of prior art is the vacuum processing apparatus shown in FIG. 1 of this application and described in U.S. Pat. No. 4,962,063 to D. Maydan et al. The vacuum processing apparatus comprises a number of deposition and etching chambers 102–108. Each of the chambers 102–108 may be used to carry out chemical vapor deposition, plasma etching, and other deposition and etching processes on a wafer normally under vacuum. Chambers 102–108 are each connected, via interlocks or slit valves 110 to a central chamber 116. The central chamber 116 houses a robot mechanism 120 for transporting the wafers within the vacuum apparatus from and to various processing chamber 102–108 and an internal wafer storage 150 (the load-lock) without breaking vacuum in the system. A supply of wafers outside the chamber is shown at 160. When a wafer completes one process in one chamber of the processing system, it can be internally transferred to another chamber for another process without leaving the vacuum system. This eliminates the need to transport the wafer through the load-lock to the other chamber. The production process is, therefore, simplified and production yield is increased. However, if the wafer needs to be inspected for particle contamination, film thickness, etching thickness or defects after each process, the wafer still has to be transferred through the load-lock to an inspection system located outside the vacuum system and operated at atmospheric (room) pressure for inspection. Such a transfer requires significant time to accomplish and reduces the advantage gained by using a multi-chamber process apparatus.

The advantages of a multi-chamber process apparatus can be fully realized if wafers can be inspected after one process while inside the processing system under the same, or similar vacuum conditions.

A processing system, such as a PVD, a CVD or an etch chamber is routinely shut down for maintenance or for a process recipe change. When the system is restarted, the conventional method of adjusting the processing system is to use so called monitor wafers. A deposition or etching process is first performed on a monitor wafer in the processing chamber. The wafer is then transferred to a wafer inspection apparatus to measure deposited particles, defects, deposition film thickness, etching thickness or the like. The information from the wafer inspection is then used to adjust the processing parameters. A typical start up for a single chamber requires processing a few to ten monitoring wafers, depending on the operating conditions and the operator's skill. A typical start up for a five-chamber vacuum process apparatus may need to process up to 50 monitor wafers, as each of the process chamber has to be individually adjusted. The start up is also a time consuming process since each of the monitor wafers has to be transferred to an outside machine for inspection after deposition or etching. The cost of using the monitor wafers is not prohibitive for small diameter wafers, which usually cost a few dollars per wafer. However, as the wafer diameter increases the cost associated with the monitor wafers significantly increases. Currently an 8 inch wafer costs approximately $30 and a 12 inch wafer costs $500 to $1,000. Reduction in monitor wafer usage is thus desired in the semiconductor device fabrication industry.

A monitor wafer is usually inspected before being loaded into the processing chamber. If an inspected monitor wafer is contaminated in a load-lock and then further contaminated in a fabrication process, a wafer inspection tool cannot distinguish how many contaminant particles are added to the wafer in the load-lock and how many are added during the fabrication step. One method to solve the problem is to leave a monitor wafer in the load lock during the process and inspect the wafer for reference. The start up time and cost for a process tool is further increased due to inaccurate information about the process contamination and the increased requirement for wafers being transferred back and forth through the load-lock between the process system and the wafer inspection tool.

The time required for a process system start up can be significantly reduced if a monitor wafer can be inspected inside the processing system. The reduction in process time is achieved by reducing the number of wafer transfers through the load-lock, which requires a pump down once for each wafer cassette transferred. The usage of monitor wafers is also reduced as the contamination risk in the load-lock is eliminated. A monitor wafer can be repeatedly used until the wafer is over loaded with particles or films. For example, assume that a monitor wafer is initially clean and undergoes a deposition process. After the deposition process if the wafer is inspected in an inspection chamber within the vacuum system and 50 particles are found on the wafer surface, it is known the 50 particles are contaminant particles deposited on the wafer during the deposition process. The processing system is then adjusted accordingly. After adjusting, the wafer is sent back to the processing chamber for another processing. When the process is finished, the monitor wafer is again sent to the inspection chamber for inspection. This time, there are a total of 75 particles found on the monitor wafer. The net addition in the second process is then 25 particles. The processing system will be adjusted again and the same monitor wafer can be used for additional tests.

In addition to scanning a wafer surface for contamination control, some methods have been developed for in-situ real time measurement of particles in process systems. U.S. Pat. No. 5,271,264 to S. Chanayem describes a method and apparatus of detecting particles in a process system exhaust. An in-situ particle monitor is placed down stream of a turbo pump for the vacuum system. However, measuring particles in an exhaust line of a process chamber gives little useful information on particles inside the vacuum process chamber. According to some industry experts, the correlation is poor between the measured particle concentration in an exhaust line and the particles deposited on a wafer after a process. U.S. Pat. No. 5,347,138 to D. Aqui describes a method using a non-invasive particle monitor to detect particles in a process chamber. In this method, a laser beam of an oval cross section is directed through a transparent window from a source outside a down sputter process chamber into the process chamber for detecting particles suspended in the plasma region during the process. Long and narrow shield tubes, each having a length of no less than three mean free paths of the gas molecules in the process chamber and a width less than one mean free path of the gas molecules in the process chamber are used to prevent metal deposition on the surface of the transparent window. Without the shield tube, the transparent window used for passing the laser beam will be soon contaminated by the metal deposition during the sputter process. However, with the shield tube, the measurement can only be made through the tube opening, whose cross sectional area is only a few square millimeters. The measurement results, therefore, do not represent the actual situation in the process chamber. The probability of generating false signal from such a measurement is high. In a semiconductor process, it is cost prohibitive to tolerate a false signal from the process tool because a false signal often results in the shut down of a process line. As described previously, re-start of a process tool is time consuming and very costly.

In some wafer processing, thin metallic and/or dielectric films are deposited on a wafer surface. The typical film deposition thickness ranges from 50 angstroms to several thousand angstroms. Knowledge of film thickness and uniformity of the thickness are desired so that the deposited layers will have the desired properties. Currently, the commonly used instrument for measuring film thickness and the uniformity of the film thickness is the ellipsometer. Most ellipsometers can not operate inside the vacuum processing apparatus for various reasons. Some in-situ measurement of film thickness methods have also been developed. U.S. Pat. No. 5,220,405 to S. Barbee describes an interferometer for measuring thin film thickness changes. U.S. Pat. No. 5,258,824 to D. Carlson et al. describes a method and apparatus used to determine the thickness of a layer deposition on a specimen. The intensity of radiation emitted by the wafer from its surface and the temperature of the silicon wafer are measured in the '824 patent. The variation in the intensity of radiation emission due to variation of the temperature is subtracted from the intensity of radiation emitted. The resultant signal is then used to calculate the thickness of the thin film.

U.S. Pat. No. 5,313,044 to H. Massoud describes a method using an ellipsometer to measure the change in polarization of light upon reflection from a wafer sample to determine the thickness of a thin film.

U.S. Pat. No. 5,450,205 to H. Sawin describes a method to measure the absolute thickness of a thin film using a CCD camera. The present invention relates to methods and apparatus to inspect wafers for particles and thin film parameters inside the vacuum system to eliminate or reduce the need for wafer transfer through a vacuum load-lock to an outside instrument for inspection.

SUMMARY OF THE INVENTION

The surface inspection system of this invention includes an inspection chamber into which the surface is introduced and which is maintained at the same or similar vacuum as the processing chamber. The inspection occurs without changing the vacuum environment. With sufficiently small components it is also possible to place the light source and light recess and associated components in the inspection chamber.

Preferably the vacuum chamber has a transparent window in at least one chamber wall to allow visible, infrared or ultraviolet light to pass between the chamber and its surroundings. A beam of light is directed onto the surface in the chamber through the window, and the scattered or reflected light from the surface through the window is detected by one or more detectors located outside the chamber. The scattered or reflected light signal is analyzed to determine the characteristics of any particles on the surface, such as particle size, or characteristics of a thin film that has been deposited on the surface during processing, such as film thickness.

To inspect a portion, or the entire surface, of a wafer by a narrow light beam, the beam must be moved relative to the wafer surface so that all parts of the area to be inspected are illuminated by the beam. The preferred method of moving the beam relative to the wafer surface is to rotate the wafer about its central axis, and linearly move the beam focus in a radial direction from the center to the edge of the wafer, or vise versa. This movement can also be accomplished by keeping the beam fixed while rotating the wafer around its axis and at the same time moving the wafer axis in a radial direction until all parts of the surface to be inspected have been illuminated by the beam. Other movements that can be used include (1) rotating the light beam around the center of the wafer and changing the radius of rotation, or (2) sweeping the beam in a fixed plane in space to illuminate a thin line on the surface, while moving the wafer past this plane until all parts of the surface to be inspected have been illuminated by the beam.

For surface inspection, either white light or laser light can be used. Laser light is preferred, because laser light can be narrowly focused on the surface to illuminate a small area with high light intensity to detect particles of a small size on the surface. The detection equipment can also be placed in an inspection chamber kept under vacuum.

The main advantage of the wafer inspection system as described above is that the wafer is inspected in a chamber kept under vacuum conditions similar to the multichamber wafer process system to which this wafer inspection chamber is attached. In the preferred form, the light source and detectors can be kept outside the chamber, and usually under atmospheric conditions. The inspection is accomplished by directing the light beam through the transparent window onto the wafer inside the inspection chamber and allowing the scattered or reflected light beam to pass back out through the transparent window to the detector(s) located outside. When processing is completed on a wafer, the wafer can be immediately transferred to the inspection chamber for inspection and returned to another processing chamber for further processing, all under the same or similar vacuum conditions.

After processing, the wafer is allowed to remain inside the system under similar vacuum conditions for inspection. Thus there is no need to transport the wafer from a vacuum to atmospheric pressure and from atmosphere pressure back into a vacuum. The wafer undergoing a multiple deposition/etching process inside a cluster process tool, therefore, does not need to be transferred to a chamber outside the machine for inspection after every processing step. The overall processing time is reduced and the risk of the wafer being contaminated during transfer from vacuum to an outside inspection machine and back into the vacuum after inspection is greatly reduced. This will result in a significant improvement in the efficiency of utilization of the processing and inspection machines, and improve the quality of the wafer products being manufactured, including improvement in product yield and reduction in the loss of yield due to product contamination by wafer transfer.

Since the monitoring wafer is inspected inside the vacuum apparatus, adjusting the tool for start up becomes more convenient and the same monitoring wafer can be used over and over to reduce the monitoring wafer usage. The results from the wafer inspection can be fed back to the processing tool directly for automatic adjustment of processing parameters.

In addition, since the present invention allows the wafer to be inspected in a separate inspection chamber, contaminants that are generated in the processing chamber can be kept separate and apart from the inspection chamber. Usually, a process chamber is sealed from the rest of the vacuum process system during processing. The inspection chamber is, thus, kept contamination free at all times. A gate valve can be installed to further guarantee inspection chamber isolation and isolation of contamination transport between chambers. The need to use a shield tube to prevent depositions onto a transparent window in a process chamber is then eliminated and the transparent window can be made large, kept clean and contaminant free, thus allowing large areas of the wafer to be inspected.

DETAILED DESCRIPTION OF THE PREFERRED EMBODIMENTS

Figure 1:
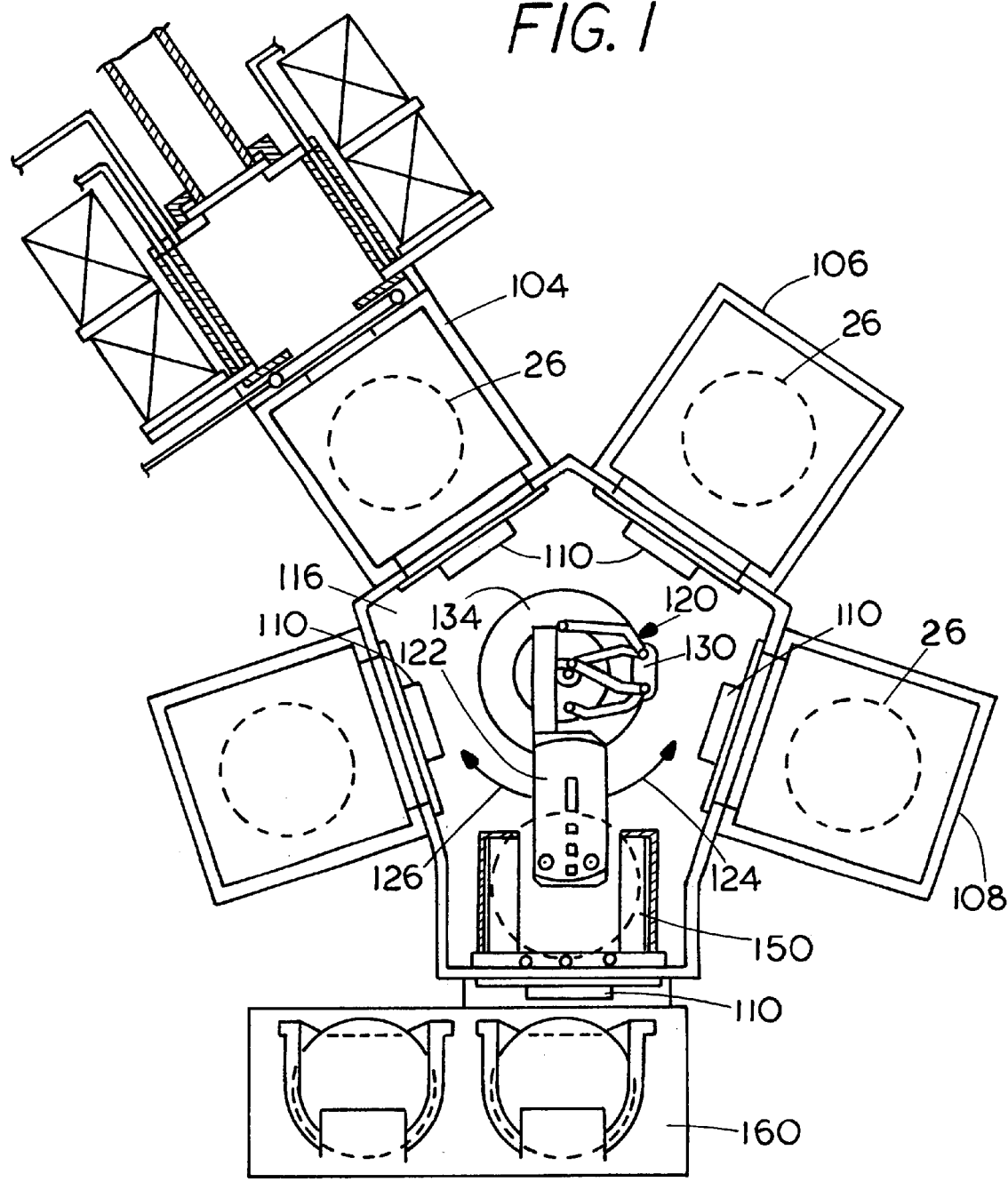
FIG. 1 is a schematic plan view of a typical prior art multiple deposition chamber apparatus.
Figure 2:
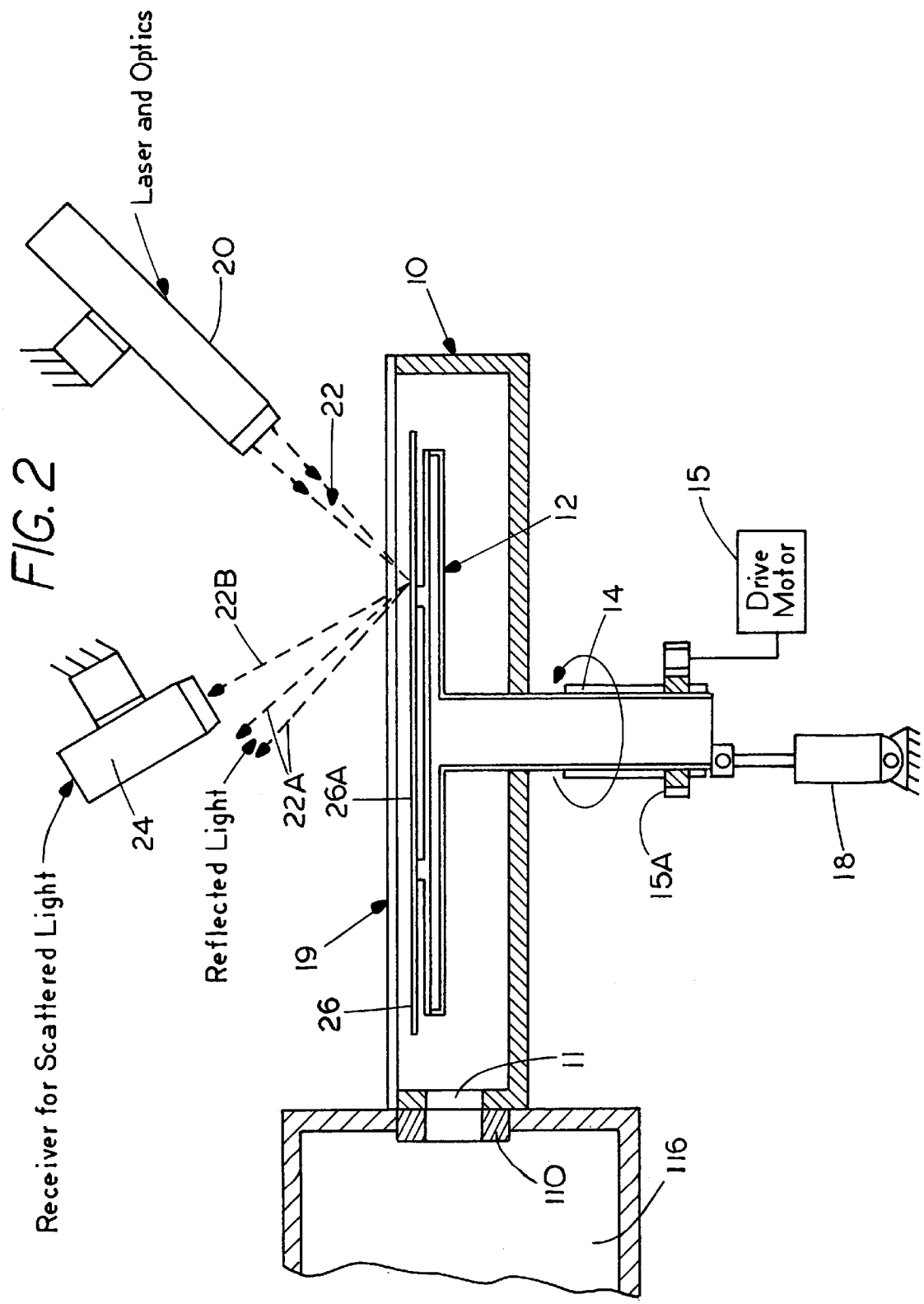
FIG. 2 is a schematic sectional view through a typical vacuum chamber used as an inspection chamber and open to a processing tool such as that shown in FIG. 1.

With reference to FIG. 2, a preferred embodiment of the present invention includes a vacuum inspection chamber 10 that is shown as being coupled to a central chamber 116, in FIG. 1. Chamber 10 replaces a chamber shown in the FIG. 1 prior art. The vacuum chamber 10 is connected through a vacuum tight slit valve or gate valve 110 alignment with a port 11. A turntable wafer or product support 12 of conventional design is positioned in the chamber 10 and is supported on a rotatable shaft 14, which is supported through a vacuum tight seal in a wall of the chamber 10. The seal permits rotating the shaft 14 with a drive motor 15 that schematically drive the shaft 14 using a ring gear and pinion set 15A. The ring gear drivably slides on shaft 14. The shaft 14 may be spliced to permit the drive to slide axially while continuing the rotationally driven.

The shaft 14 also can be moved axially to raise and lower the support. An actuator 18 is shown schematically for raising and lowering the support 12.

The drive for rotating the shaft 14 and the actuator shown for raising and lowering the wafer are shown very schematically. A stepper motor and small actuator may be placed inside the vacuum chamber and operate from external controls. That would eliminate the need for a rotary vacuum seal on shaft 14. A stepper motor can be used to directly drive the shaft 14.

The top wall of the chamber 10 is covered with a transparent plate or window 19 made, for example, of quartz or glass. A laser source and optics assembly 20, providing a laser beam 22 is mounted on a bracket on the exterior of the chamber 10. A receiver for scattered light is also mounted in position to sense scattered light 24. The vacuum inspection chamber 10 is connected to chamber 116 of a vacuum process tool such as that shown in FIG. 1 and replaces chamber 108, for example. The opening 11 allows a wafer or other product 26 being transferred from the vacuum process tool chamber 116 to the vacuum inspection chamber 10 without breaking the vacuum.

During the process of wafer transfer, the wafer support 12 is vertically lowered by operating actuator 18 to a level at which a wafer from chamber 116 can be transferred via a robot arm, such as that shown in FIG. 1 at 120, through a slit valve 110 and opening 11 into the space above the wafer support 12. The wafer support 12 then is gradually lifted to support the wafer 26. When the wafer support is supporting the wafer 26, the wafer transfer robot arm 120 withdrawn from the vacuum inspection chamber 10 via the opening 11. The wafer support 12 will then continue to be moved upwardly until the laser beam 7 is in focus with the wafer top surface 26A. Alternatively, the laser and optics assembly 20 and the receiver for scattered light 25 can move up and down for focusing on the wafer surface. The vacuum inspection chamber 10 is under the same or similar vacuum as the vacuum chambers 102–108 and 116 of the process tool.

A laser beam source 20 comprising a laser and optics assembly is shown schematically since it consists of a commercially available single wavelength laser, and a set of optics, including a reflective mirror and a set of focusing lens. Multi-wavelength lasers can be also used to replace the single wavelength laser.

The transparent plate 19 seals the vacuum inspection chamber 10 from the ambient environment where the laser and optic assembly 20 and the scattered light receiver 24 are located. The scattered light receiver 24 also is a conventional commercially available unit useful for determining the light scattered by particles or imperfections on the wafer surface 26A. The laser source and optic assembly and the receiver 24 for scattered light including the laser, the receiver and optics can then operate at a higher pressure, preferably at atmospheric pressure. The vacuum inspection chamber 10 can then be made very compact, just large enough to house the wafer 26 to be inspected.

When the laser beam indicated at 22 impinges upon the wafer surface 26A, the reflection path from a smooth, clean surface is represented by lines 22A, but a fraction of the incident beam is scattered by particles, or by haze or imperfections on the wafer surface within the beam focusing area. The scattered light represented by lines 22B is then directed to the scattered light receiver 24. There are many ways to direct the scattered light to a receiver. One method similar to that described in U.S. Pat. No. 4,378,159 to L. Galbraith uses an integrating sphere, which is a hollow sphere with its inside surface coated with a reflective material to reflect the scattering light to a photomultiplier for beam collection. An electrical signal representing the intensity of the scattered light is generated and transmitted through wires to a receiver.

Figure 3:
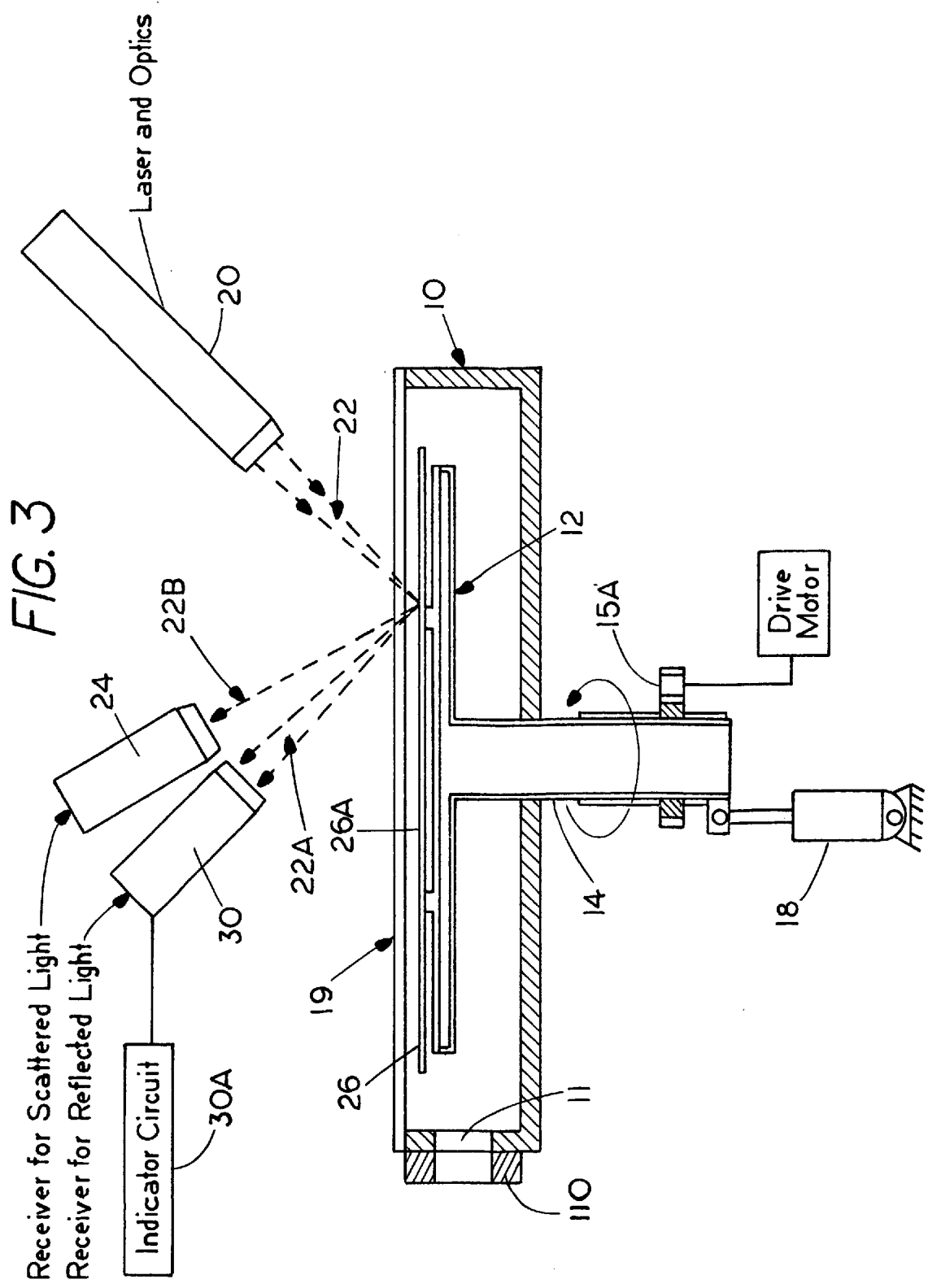
FIG. 3 is a sectional view similar to that shown in FIG. 2, but also including a receiver for receiving reflected light.

FIG. 3 illustrates the apparatus shown in FIG. 2, but adds a light receiver 30 for receiving reflected light shown by lines 22A. Reflected light means a light beam reflection where the angle of reflection equals the angle of incidence. Thus reflected light indicates a surface of coating that does not have particles or imperfections on or in it. The light receiver 30 consists of a set of apertures and a light detector. A CCD detector may also be used as the receiver 30 as well as a linear detector. These types of receivers 30 are all commercially available. The additional receiver 30 is used in film deposition systems primarily where light passes through the deposited film. The reflected light is collected and then converted to an electrical signal in the receiver 30 which is transmitted via wires to an indicator circuit 30A. The signals from the receiver for normal reflection are indicative of film thickness and thus can be used for film thickness measurement in a film deposition system. U.S. Pat. No. 5,416,594 to K. Gross et al. describes a method of using reflected light signals to calculate the thickness of a thin film.

Figure 4:
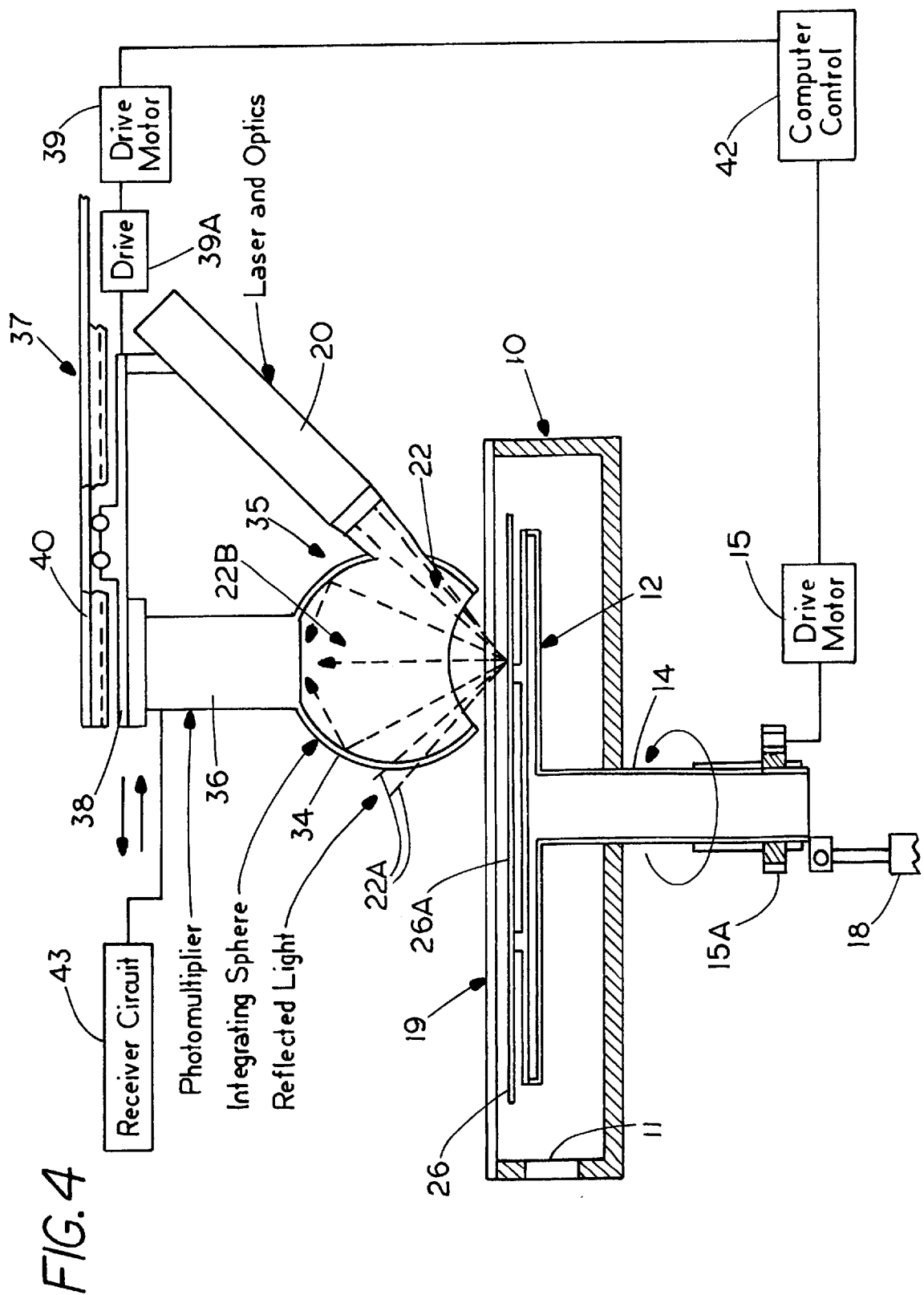
FIG. 4 is a modified preferred embodiment of the present invention showing an inspection chamber using a laser source and an integrating sphere assembly for inspection.

FIG. 4 shows another modified preferred embodiment of the present invention which includes a vacuum inspection chamber 10, a wafer support 12, a transparent plate 19 covering the interior of the chamber, a laser source 20 providing a laser beam 22. In this form of the invention a particle detection assembly 37 is mounted for linear movement, and a receiver for scattered light 35 is different from the forms of FIGS. 2 and 3. The receiver 35 includes an integrating sphere 34 and a photomultiplier 36 mounted on a carriage 38 which in turn is supported on a track 40. The carriage is driven with a reversible drive motor 39 through a suitable chain or screw drive 39A.

The laser source 20 in this form of the invention is also mounted on carriage 38 so the laser source 20, the integrating sphere 34 and the photomultiplier assembly 36 are mounted at fixed positions relative to each other. The carriage 38 and track 40 permit linear motion across the transparent plate 19.

During a wafer scan, the wafer 26 which is supported by the wafer support 12 is rotated while the laser source 20 and reflected light receiver 35 are moved linearly. The rotational speed of support 12 and the linear motion speed of the carriage 38 are controlled by using a computer 42 to drive the motors 15 and 39 and correlate the speeds, such that a constant scanning speed across the entire wafer surface 26A to be inspected is provided.

During a scan, the integrating sphere 34 redirects all scattered light caused by particles or haze within the laser beam impingement area to the photomultiplier assembly 36, which converts the light signal to an electrical signal and sends the signal via wires to a receiver circuit 43. The particle count and size are then calculated in the receiver circuit or in a separate computer based on the integrated scattered light signals, using known techniques.

Figure 5:
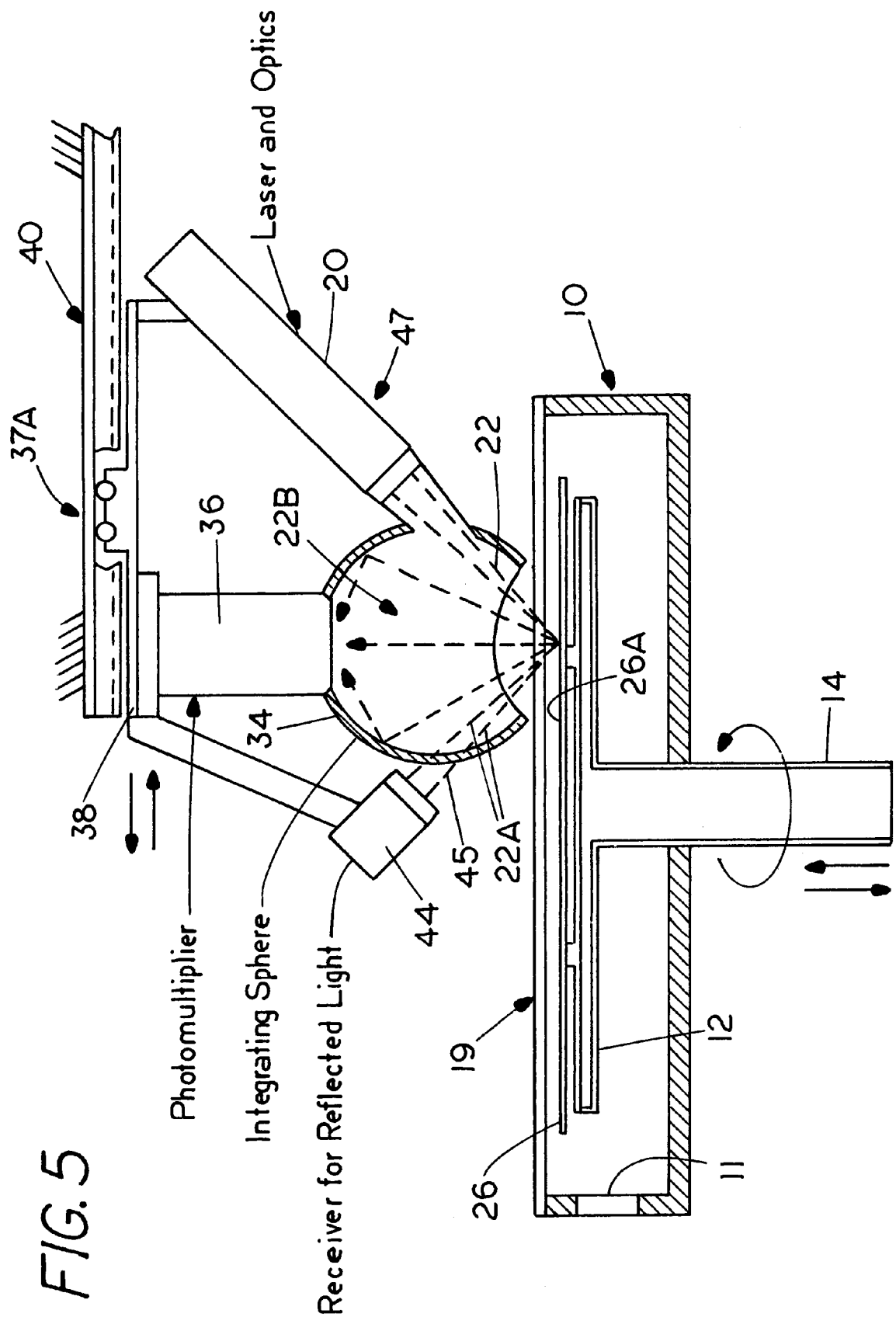
FIG. 5 is a sectional view similar to that shown in FIG. 4, but including a receiver for reflected light.

FIG. 5 is an illustration of a modified form of FIG. 4, and in addition to the components described in FIG. 4 the particle detection assembly 37A includes a light receiver 44 is mounted on carriage 38 for collecting the normal reflected light through a transparent window 45 on the integrating sphere 34 for providing additional information about particles and film thickness on the wafer 26. The window 45 is positioned in the known path of normal reflected light. The particle detection assembly 47 including the laser source 20, the integrating sphere 34, the photomultiplier assembly 36 and the light receiver 44 for receiving normal reflected light is mounted on the carriage 38. The components are mounted at fixed positions relative to each other.

The particle detection assembly 47 is supported on track 40 for transverse linear motion relative to a wafer 26 in chamber 10. During a scan of wafer 26 on wafer support 12 in chamber 10, the support and wafer are rotated while the particle detection assembly 47 is moved along the track 40. The rotational speed of motor 15 and thus of the wafer 26, and the speed of motor 39 providing the linear motion are controlled and synchronized with computer 42 such that a constant speed scan is made across the entire wafer surface 26A to detect particles or haze within the laser beam impinge area. Scattered light is detected by the photomultiplier assembly 36. The photomultiplier converts the light signal received to an electrical signal and sends the electrical signal via wires to a receiver circuit 43. The light beam receiver 44 converts the normal reflected light into an electrical signal and sends the signal via wires to an indicator circuit 30A. The particle count and the size of the particles on the surface 26A of wafer 26 are then calculated based on the integrated scattered light signals. The signal from the receiver receiving reflected light is used to calculate film thickness.

Figure 6:
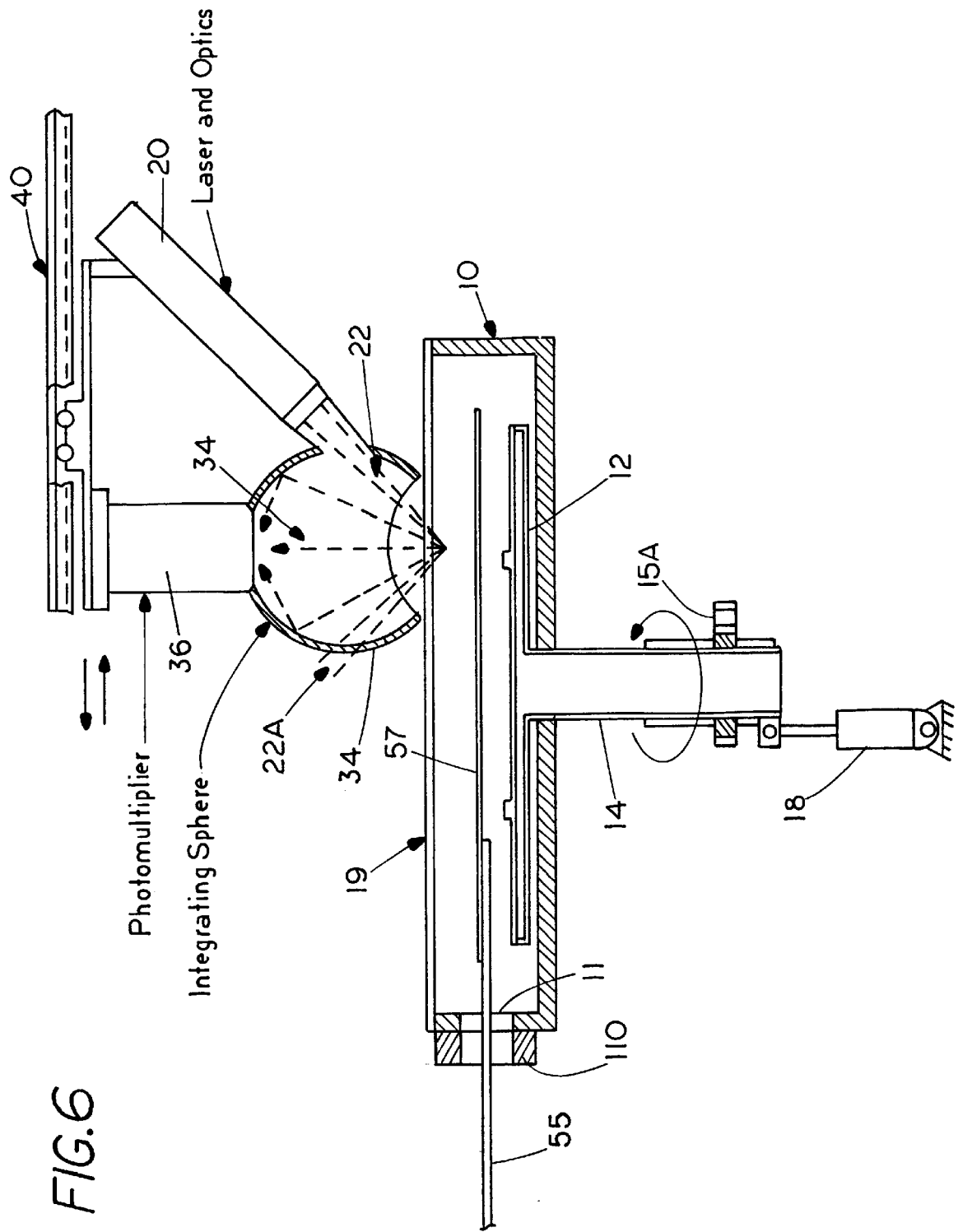
FIG. 6 is a sectional view of an inspection chamber similar to FIG. 4 and including a linear motion assembly or arm as shown in the prior art for transferring the wafer into the inspection chamber.

In FIG. 6, the wafer support 12, which comprises a rotatable turntable as described, is shown in a lowered position, with the actuator 18 retracted. Again, the actuator 18 is merely a schematic showing of a device that can be used for raising and lowering the turntable while permitting the turntable to be rotated by its drive motor 15 through a gearset 15A.

In this form of the invention, a robot arm 55, which corresponds to the robot arm 122 shown in FIG. 1, is supporting a wafer 57, and it has inserted the wafer through the opening 11 and a suitable slit valve 110. This operation using a robot arm for handling the wafers is carried out in a normal operation when a wafer is to be transported from the central chamber shown in FIG. 1 at 116 to one of the satellite chambers 102–108. In this instance, the chamber 10 is being provided with the wafer utilizing a robot arm that is on existing equipment.

Once the wafer is within the chamber 10, as shown in FIG. 6, the wafer support 12 will be raised by operating the actuator 18, and then the controls will cause the robot arm to withdraw, and the operations can take place as previously described. The laser source 20 is the same as that shown in FIG. 4, and the operations can be conducted as explained in connection with FIG. 4.

Figure 7:
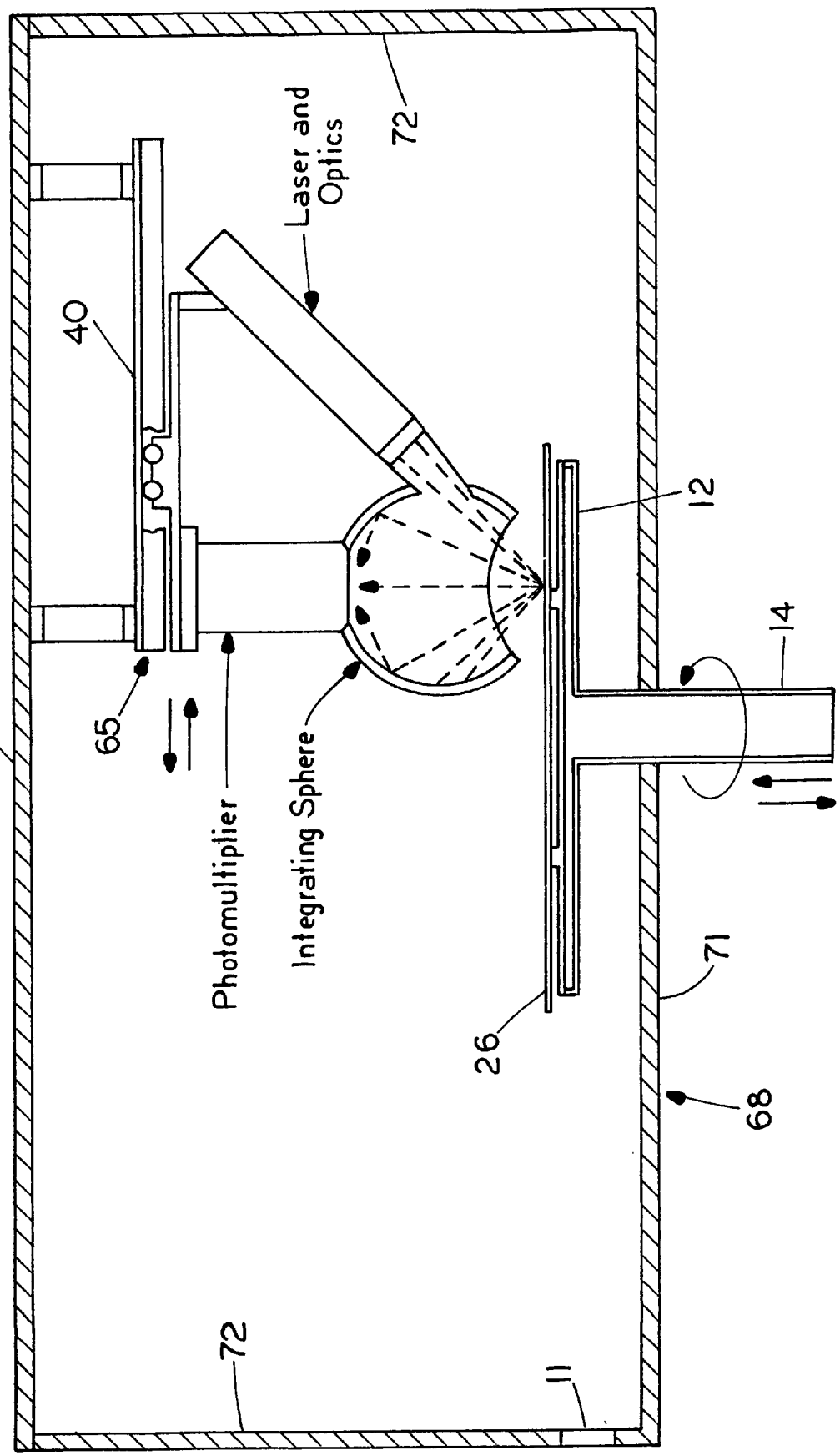
FIG. 7 is a modified form of the invention wherein the light detecting assembly and the linear motion assembly for inspection are entirely within a vacuum inspection chamber.

In FIG. 7, a system for detecting particles 65 such as that shown in FIG. 4, including the carriage 38, the photomultiplier 36, the integrating sphere 34, the laser source 20, and the other components are exactly as shown therein, but the chamber 68 is modified. The chamber 68, as shown, is enlarged to completely enclose the system 65 as well as the wafer support 12 and the wafer 26. The inlet opening or port 11 is located in the same position relative to the lower wall of the chamber, but the chamber is increased substantially in size in all dimensions and includes a lower wall 71, sidewalls 72, and a top wall 70 that are completely enclosed. The interior of the chamber will be subject to vacuum.

When the entire assembly is within a vacuum chamber, as shown, inspection can be carried out as previously described, but the chamber has to be substantially enlarged and all of the components used for inspection such as the laser source and optics, receivers, and the in form shown the photomultiplier and the integrating sphere are all subjected to vacuum.

Figure 8:
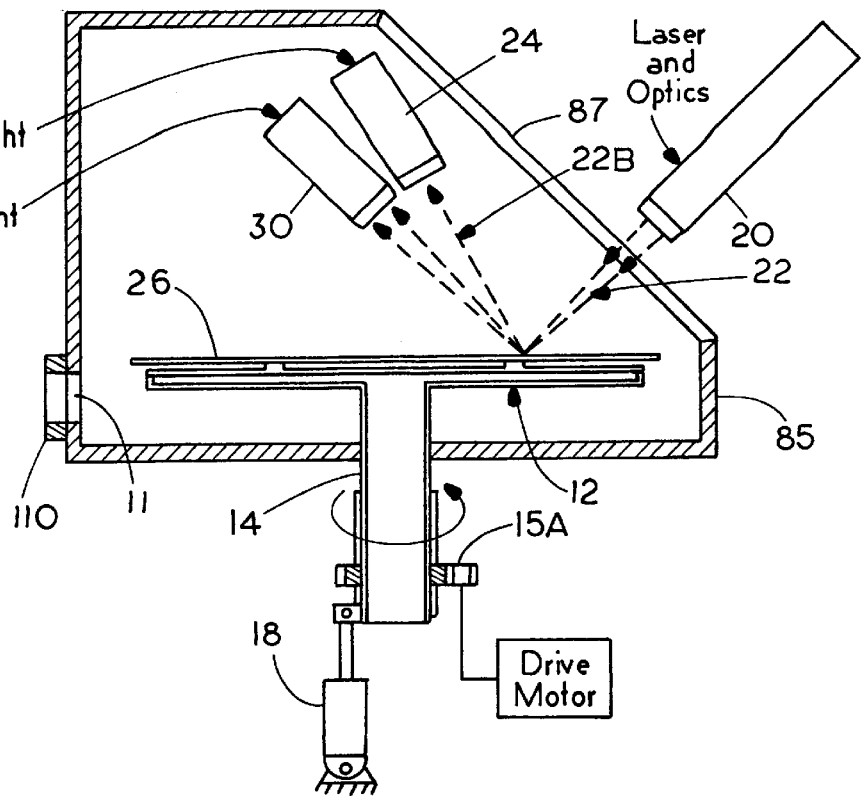
FIG. 8 is a schematic sectional view of a chamber wherein the light detecting assembly is positioned within the vacuum inspection chamber, and the light source is on the exterior.

In FIG. 8, a modified arrangement is shown where an inspection chamber 85 is formed, and it is larger than the chamber 10, but also is connected to the central chamber 116 of a vacuum processing apparatus such as that shown in FIG. 1. In this form of the invention the light source, comprising a laser source and optic assembly 20 is mounted on the exterior of the chamber 85. The laser beam 22 is passed through a light transparent window 87 in chamber 85. In this form of the invention the light receivers, which are the same as shown in FIG. 3, comprising a reflected light receiver 30 and a scattered light receiver 24, are both inside the chamber 85 and under vacuum when inspection is taking place. The signals can be carried on lines that have vacuum seals where they pass through the chamber walls. The components for operation of the inspection apparatus, and the rotating elements as well as the lifting and lowering of the product support are the same as in FIG. 3.

Figure 9:
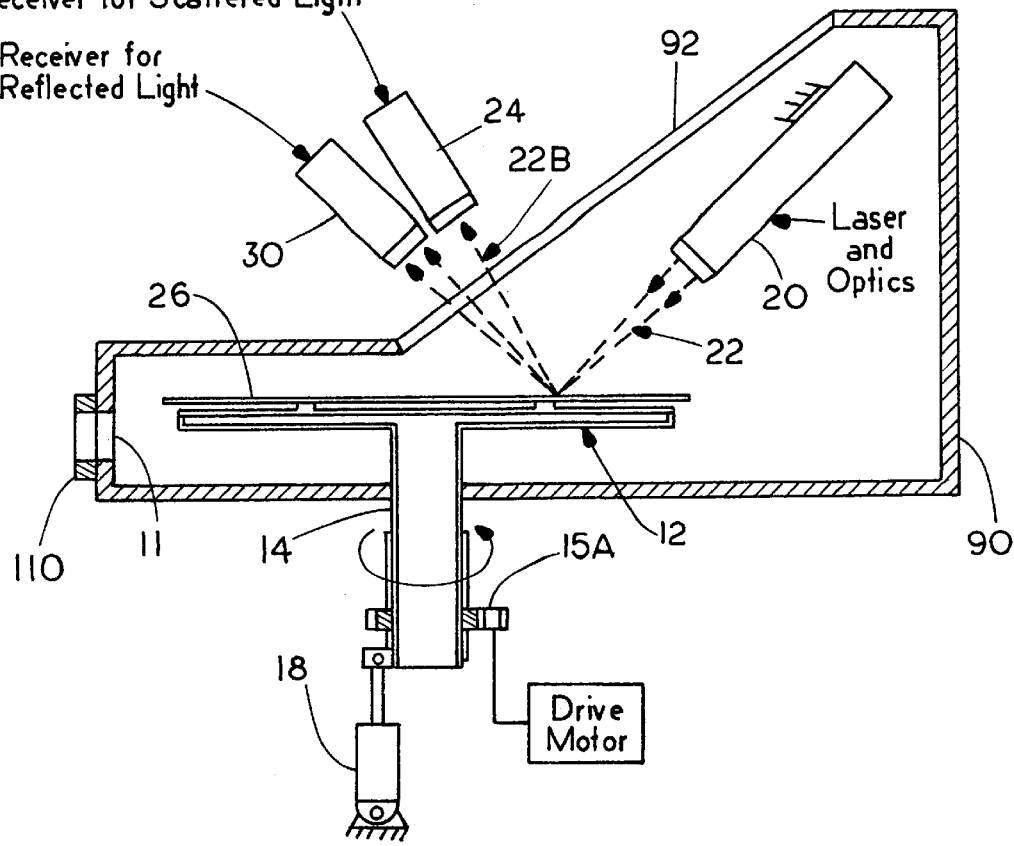
FIG. 9 is a sectional view of a chamber wherein the light source is positioned on the interior of the vacuum inspection chamber and the light detecting assembly are on the exterior of the vacuum inspection chamber.

FIG. 9 is a modification of FIG. 8 and includes a vacuum inspection chamber 90, which is connected to chamber 116 of the vacuum processing apparatus shown in FIG. 1. In this form the light or laser source comprising the laser and optic assembly 20 is inside the vacuum inspection chamber 90. The reflected light receiver 30 and scattered light receiver 22 are outside the chamber 90, and receive the scattered light and reflected light through a light transparent window or wall 92. The components for performing the inspection are not under vacuum, while the light source is.

When using the chambers of FIGS. 8 and 9 the inspection is carried out without moving the wafer 26 to atmospheric pressure between the processing system and the inspection chamber.

In all forms of the invention, the inspection takes place in a chamber that is connected to the same vacuum system as the processing chamber so that the inspection chamber is maintained under a vacuum and the wafer does not have to be passed through an air lock arrangement and brought up to atmospheric pressure for inspection and then brought back down to an environment of vacuum for further processing.

FIG. 1 shows the typical arrangement for loading and unloading wafers, and this type of a processing system is well known in the prior art.

Although the present invention has been described with reference to preferred embodiments, workers skilled in the art will recognize that changes may be made in form and detail without departing from the spirit and scope of the invention.

What is claimed is:

1. A processing and inspection apparatus including at least one product processing chamber for processing a product under vacuum, the product having a flat surface, at least one vacuum source for maintaining the product under vacuum, and an inspection chamber under vacuum, the inspection chamber including a wall that has a portion capable of transmitting light, and inspection equipment for the product comprising a light source and reflected light receiver positioned on the exterior of said inspection chamber to direct light onto a product and receive reflected light from a product, a transfer device for transferring the product from the processing chamber to the inspection chamber, said inspection equipment being operable to carry out inspection for contaminate particles on the flat surface of a product transferred from the processing chamber to the inspection chamber while the product remains under vacuum at all times during processing, transferring and inspection of the product.

2. The apparatus of claim 1, wherein said light source comprises a laser light source for providing a focused area on the product.

3. The apparatus of claim 1, wherein the product comprises a semiconductor wafer and a support for the product on the interior of the inspection chamber, a drive to rotate said support to rotate the product about an axis within the chamber.

4. The apparatus of claim 3 including a mounting for the light source and reflected light receiver for providing linear motion transverse to an axis of rotation of the product, the light source and the reflected light receiver moving linearly laterally across the product as the product rotates.

5. The apparatus of claim 4 and control means to synchronize rotation of the product and the linear motion of the light source and reflected light receiver.

6. The apparatus of claim 5, wherein the reflected light receiver comprises a first receiving portion for light that is reflected from a smooth surface on the product and a second receiver portion for light reflected and scattered.

7. The apparatus of claim 5, wherein the reflected light receiver comprises an integrating sphere.

8. The apparatus of claim 1, wherein said inspection chamber comprises a wall that has a portion capable of transmitting light, and a light source and reflected light receiver positioned on the exterior of said inspection chamber to direct light onto a product in the inspection chamber and receive reflected light from such a product for inspection purposes.

9. A processing apparatus for a product having a substantially flat surface on which a process is performed under a vacuum comprising a plurality of chambers positioned adjacent to each other and having access passages therebetween, the chambers and the access passages all being fluidly open to each other and under the same vacuum, a first of said chambers being a processing chamber for performing a process on the flat surface, and a second of said chambers comprising an inspection chamber for inspecting the flat surface, a product support in each of the chambers, and a transfer mechanism within at least one of the chambers and the passage for transferring the product from the first chamber to the second chamber without opening either of the chambers to atmosphere, the second chamber comprising an inspection chamber having a wall portion capable of transmitting light, that reflects from the flat surface, said inspection equipment including a laser light source and a detector, both mounted on the exterior of the inspection chamber, the laser directing light onto the flat surface which reflects light out of the chamber through the wall portion and the detector being mounted to receive reflected light and detect changes in the reflected light due to presence of contaminate particles on the flat surface.

10. The apparatus of claim 9 including a wall formed in the second chamber having a wall portion capable of transmitting radiant energy that reflects from the flat surface, said inspection equipment including a source of radiant energy and a detector for detecting radiant energy positioned to determine when reflected radiant energy is affected due to changes in a characteristic of the flat surface.

11. The apparatus of claim 9, wherein the laser light source includes an optic assembly for providing a focused area of a laser beam onto the product, said detector being positioned to receive reflected light and provide a signal indicating the amount of reflected light.

12. A method of processing and inspecting a wafer having a flat surface on which a film is deposited in a first chamber, comprising the steps of providing a second chamber having a light transmitting wall portion connected to the first chamber, providing vacuum in both chambers and on the wafer while transporting the product from the first to the second chamber, and mounting inspection equipment comprising a light source and a reflected light detector on an exterior of the second chamber at ambient atmospheric pressure and performing the inspection through the light transmitting wall portion by directing light onto the flat surface of a wafer in the second chamber and detecting when a change in reflected light indicates a contaminate particle on the flat surface.

13. The method of claim 12, wherein the inspecting step comprises moving the inspection equipment linearly to move the light across the wafer and simultaneously rotating the wafer about an axis perpendicular to the linear movement.

\* \* \* \* \*